United States Patent [19]

Attison

[11] Patent Number: 5,072,462

[45] Date of Patent: Dec. 17, 1991

[54] ROTATING POSITIONING PLATFORM

[76] Inventor: Daniel J. Attison, 139 Commack Rd., North Babylon, N.Y. 11703

[21] Appl. No.: 637,740

[22] Filed: Jan. 7, 1991

[51] Int. Cl.$^5$ .............................................. A61G 7/00
[52] U.S. Cl. ............................................ 5/60; 5/414; 5/425; 5/508
[58] Field of Search .................. 5/1, 60, 284, 400, 401, 5/414, 423, 425, 474, 508; 128/376; 272/28 R, 28 S, 39, 42, 43, 46

[56] References Cited

U.S. PATENT DOCUMENTS

| | | | |
|---|---|---|---|
| 869,772 | 10/1907 | Coderre | 5/60 |
| 972,310 | 10/1910 | Wintermute . | |
| 1,041,187 | 10/1912 | Steinert . | |
| 1,389,480 | 8/1921 | Berman | 5/60 |
| 1,739,725 | 12/1929 | Lamar . | |
| 2,877,827 | 3/1959 | Anderson . | |
| 2,993,216 | 7/1961 | Casey | 5/414 |
| 3,075,762 | 1/1963 | Ahrens . | |
| 3,397,881 | 8/1968 | Hedgecock | 272/46 X |
| 3,588,098 | 6/1971 | Stewart . | |
| 3,803,646 | 4/1974 | Newerowski | 5/474 X |
| 4,140,128 | 2/1979 | Van DerSchaaf | 128/376 |
| 4,286,344 | 9/1981 | Ikeda | 5/474 X |
| 4,607,401 | 8/1986 | Sisson | 5/414 |
| 4,903,353 | 2/1990 | Park | 5/284 X |

Primary Examiner—Michael F. Trettel
Attorney, Agent, or Firm—Leonard Belkin

[57] ABSTRACT

A rotating positioning platform apparatus for providing stimultion to a client population consisting of non-ambulatory persons having a mental age in the range of zero to five years. The apparatus consists of a rotating platform having a mattress therein and a bolster mounted on the periphery thereof to permit one or more of said persons to be placed and remain comfortable. A pole and canopy is mounted above said rotating platform. Under the canopy there are formed a number of quadrants each one of which is provided with a source of stimulation such as feel, sight, and sound. As the platform is rotated the person thereon is subject to each different kind of stimuli in sequence when the pole is stationary.

8 Claims, 1 Drawing Sheet

ROTATING POSITIONING PLATFORM

BACKGROUND OF THE INVENTION

This invention relates to a rotating positioning platform and more particularly to a platform which is designed to enhance the quality of life for non-ambulatory persons offering motion and sensory stimulation.

In recent years there has been increased interest in improving the quality of life of those members of a population who are non-ambulatory, having a mental age from zero to five years, and typically, having a body weight in the range of 65 to 110 pounds. These persons may have been born with such defects, or suffered post natal trauma resulting in such a condition. Physically, they may be paraplegic, suffer paralysis of lower extremeties, have constriction of limbs due to shortening of tendons, or suffer muscle atrophy, among other related physical disorders.

In the past, such patient population were warehoused and they received virtually no meaningful care. Living conditions were austere at best and abysmal at worst. No attempts or efforts in most facilities were made to improve or establish a minimum quality of life for this population. As a result of a series of exposes several years ago disclosing to the public for the first time the conditions under which these persons were being cared for there has been increased interest in improving their living conditions.

Rotating platforms or carousels for amusing children are known in the art. A number of patents have been issued over the years for such apparatus.

U.S. Pat. No. 972,310 shows ammusement apparatus consisting of a portable skating rink, which is stationary.

U.S. Pat. No. 1,041,187 illustrates a roundabout mounted on rollers with provision for passengers to be seated.

U.S. Pat. No. 1,739,725 discloses a merry-go-round suspended from a central post with seats on the outside.

U.S. Pat. No. 2,877,827 shows a rotatable table with seats on the outside.

U.S. Pat. No. 3,075,762 illustrates a merry-go-round with provision for the passengers to stand or sit along the outside in depressions.

U.S. Pat. No. 3,588,098 shows an amusement apparatus in which a flexible outer wall is employed on which children can play as the apparatus rotates.

None of the preceding patents discloses or suggests the present invention nor are any of them suitable for use with the patient population herein described.

SUMMARY OF THE INVENTION

In this invention there is provided a rotating positioning platform designed specifically to enhance the quality of life for non-ambulatory persons of limited mental capacity offering motion and sensory stimulation.

A preferred embodiment of this invention consists of a circular platform mounted for rotation having a padded floor with the entire perimeter featuring a permanently installed bolster wedge serving as a head rest and to guard against accidental falls.

An adaptive stimulation canopy may be provided which is self supporting dividing the platform into several quadrants in which each quadrant provides a discreet stimulation device such as a fan, a radio, a mirror, and a mobile.

It is thus a principal object of this invention to provide a rotating positioning platform offering sensory and motion stimulation for non ambulatory persons with limited mental capacity.

Other objects and advantages of this invention will hereinafter become obvious from the following description of preferred embodiments of this invention.

DESCRIPTION OF THE PREFERRED EMBODIMENT

Figure 1:
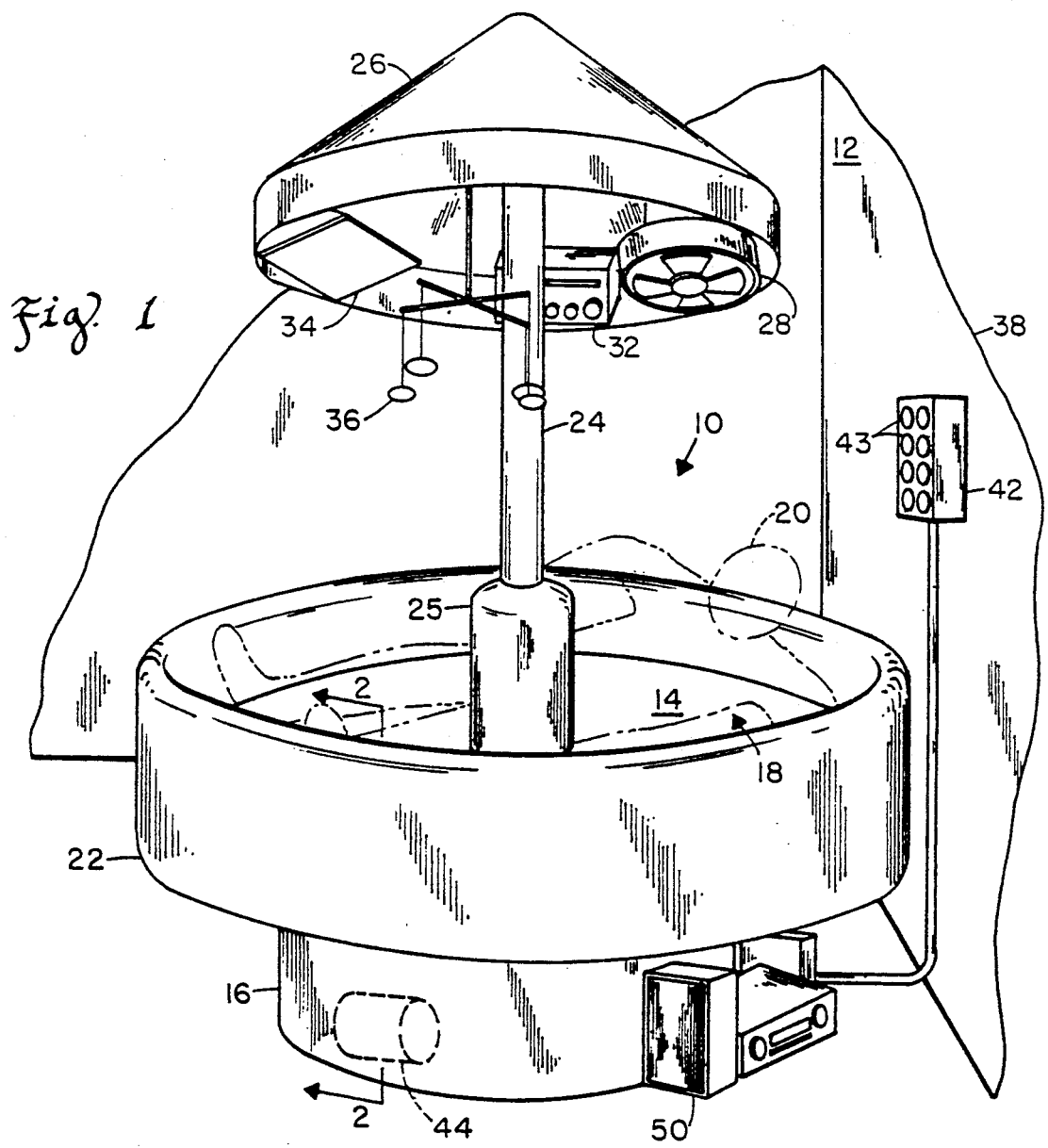
FIG. 1 is a perspective view of a preferred embodiment of this invention.
Figure 2:
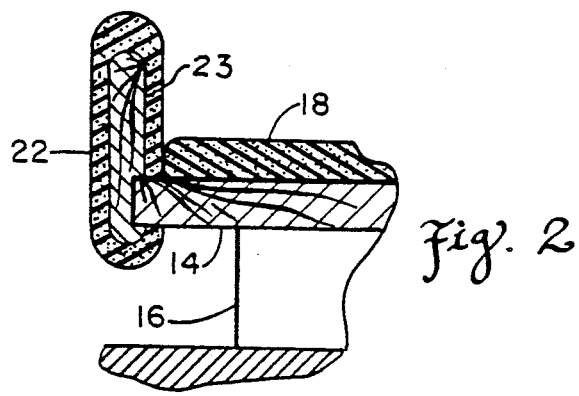
FIG. 2 is a section view taken along 2—2 of FIG. 1.

Referring to FIGS. 1 and 2, rotating positioning platform 10 is mounted within room 12 and consists of a rotatable circular platform member 14 mounted on a stationary base 16.

Platform member 14 is circular and located thereon is a mattress 18. Along the rim or periphery of platform member 14 is mounted a bolster 22 which is an extended member cushion of soft, cushion material such as foam rubber covered with a fabric or synthetic or natural leather on a rigid frame 23. It will be seen that bolster 22 extends both below and above mattress 18 and platform member 14 so that a patient 20 lying on mattress can rest his or head on bolster 22.

In the center of platform member 14 extending upwardly is a pole 24 passing through a pedestal 25 supporting a canopy 26. Pedestal 25 is attached to and rotates with platform member 14. Pole 24 passes through pedestal 25 and may either rotate along with platform member 14 or be stationary, to be determined by the operator. Canopy 26, being attached to pole 24, will rotate when pole 24 rotates and remain stationary when when pole 24 is stationary.

The space below canopy 26 is divided into four quadrants. In one quadrant is mounted an electric fan 28. in a second quadrant is mounted a radio or tape player 32, in a third quadrant is mounted a downwardly facing mirror 34, while a mobile 36 is suspended in the fourth quadrant.

Mounted on one wall 38 of room 12 adjacent rotating positioning platform 10 is a switch panel 42 in which is located switches 43 to control the starting and stopping of platform member 14, the operation of pole 24 (whether it is stationary or rotates), the operation of electric fan 28, and radio or tape player 32. If desired, remote control and variable speed switches may be provided.

Base 16 contains an electric motor 44 which through a belt drive or other transmission (not shown) would effect the rotation of both or just platform member 14 and pole 24. A music system 50 may be placed adjacent base 16 if desired.

The drive mechanisms are conventional and do not form a part of this invention.

In the operation of rotating positioning platform 10 just described, normally pole 24 would be left stationary. The patient would be placed on platform member 14 as shown in phantom and platform 14 would then be energized from switch panel 42 to rotate. If radio 32 and fan 28 are turned on then patient 20 would pass under each quadrant, passing under fan 28, radio 32, mirror 34, and mobile 36 in sequence and being subject to a variety of stimuli, i.e., feel (draft from the fan), sound, and sight.

Up to three or four patients may be placed on the apparatus at one time, and in addition to the client population described, may be used with cerebral palsy children of average intelligence.

Apparatus of the type herein described has been built and put into use with the type of the client population as hereinabove described.

While only certain preferred embodiments of this invention have been described, it is understood that many variations thereof are possible without departing from the principles of this invention as defined in the claims which follow.

What is claimed:

1. Rotating positioning apparatus for use with a client population consisting of non-ambulatory patients having a mental age in the range of zero to five years, for subjecting said patients to a variety of stimulii comprising a stationary base means supporting a rotatable platform circular in configuration, mattress means located on the top of said platform, a bolster of cushion-like construction mounted along the complete outer periphery of said platform extending above said mattress means and below said platform, vertical pole means extending up through the center of said platform supporting at the top thereof a canopy, said canopy being divided into a plurality of quadrants in which are mounted a source of a stimulation in each of said quadrants.

2. The apparatus of claim 1 in which said canopy remains stationary while said platform with a patient thereon rotates.

3. The apparatus of claim 2 in which the sources of stimulation include a fan for feel, a sound source, and a source of visualization.

4. The apparatus of claim 3 in which said vertical pole means passes through a pedestal which rotates with said platform.

5. The method of subjecting a client population to a variety of stimulii, said population consisting of nonambulatory persons who have a mental age in the range of zero to five years, placing one or more of said persons on a rotating positioning apparatus consisting of a stationary base means supporting a rotatable platform circular in configuration, mattress means located on the top of said platform on which said persons are placed, a bolster of cushion-like material mounted along the complete outer periphery of said platform extending above said mattress and below said platform for providing additional support for said persons, vertical pole means extending up through the center of said platform supporting at the top thereof a canopy, said canopy being divided into a plurality of quadrants each of which contains a source of stimulation, said person being placed on said mattress means with his head resting on said bolster means, energizing said base means to rotate said platform so that said person rotates and is subject to at least one source of stimulation.

6. The method of claim 5 in which said canopy remains stationary while said platform rotates so that said patient passes through said quandrants and is subject to a plurality of stimulii in sequence.

7. The method of claim 6 in which the sources of stimulation include a fan for feel, a sound source, and a source of visualization.

8. The method of claim 7 in which said vertical pole means passes through a pedestal which rotates with said platform.

* * * * *